(12) United States Patent
Kim et al.

(10) Patent No.: US 6,736,777 B2
(45) Date of Patent: *May 18, 2004

(54) BIOSENSOR, IONTOPHORETIC SAMPLING SYSTEM, AND METHODS OF USE THEREOF

(75) Inventors: Lynn Kim, Walnut, CA (US); Norman A. Parris, Belmont, CA (US); Russell O. Potts, San Francisco, CA (US); Michael J. Tierney, San Jose, CA (US)

(73) Assignee: Cygnus, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/353,734

(22) Filed: Jan. 29, 2003

(65) Prior Publication Data

US 2003/0135100 A1 Jul. 17, 2003

Related U.S. Application Data

(63) Continuation of application No. 09/267,750, filed on Mar. 10, 1999, now Pat. No. 6,587,705, which is a continuation-in-part of application No. 09/174,902, filed on Oct. 19, 1998, now abandoned.

(60) Provisional application No. 60/080,591, filed on Apr. 3, 1998, and provisional application No. 60/077,993, filed on Mar. 13, 1998.

(51) Int. Cl.$^7$ ................................. A61B 5/00
(52) U.S. Cl. ........................ 600/365; 600/347
(58) Field of Search ............... 600/345–350, 600/573

(56) References Cited

U.S. PATENT DOCUMENTS

| | | | |
|---|---|---|---|
| 3,173,885 A | 3/1965 | Short et al. | |
| 4,933,062 A | 6/1990 | Shaw et al. | |
| 4,970,145 A | 11/1990 | Bennetto et al. | |
| 4,975,581 A | 12/1990 | Robinson et al. | |
| 5,036,861 A | 8/1991 | Sembrowich et al. | |
| 5,076,273 A | 12/1991 | Schoendorfer et al. | |
| 5,086,229 A | 2/1992 | Rosenthal et al. | |
| 5,139,023 A | 8/1992 | Stanley et al. | |
| 5,140,985 A | 8/1992 | Schroeder et al. | |
| 5,231,028 A | 7/1993 | Mullen | |
| 5,262,035 A | * 11/1993 | Gregg et al. | 204/403.11 |
| 5,267,152 A | 11/1993 | Yang et al. | |
| 5,279,543 A | 1/1994 | Gilkfeld et al. | |
| 5,362,307 A | 11/1994 | Guy et al. | |

(List continued on next page.)

FOREIGN PATENT DOCUMENTS

| | | |
|---|---|---|
| EP | 0 247 850 | 12/1987 |
| EP | 0 942 278 B1 | 6/2002 |

(List continued on next page.)

OTHER PUBLICATIONS

Tierney et al., "*In Vivo* Performance of a Continual, Transdermal Glucose Monitoring System," presented at: 30$^{th}$ Annual Oak Ridge Conference, Apr. 23–24, 1998; meeting topic: "Miniaturization of Analytical Systems".

(List continued on next page.)

*Primary Examiner*—Robert L. Nasser
(74) *Attorney, Agent, or Firm*—Barbara G. McClung; Gary R. Fabian

(57) ABSTRACT

The present invention relates generally to a sensor for use in monitoring the amount or concentration of target chemical analytes present in a biological system. For example, the invention relates to a sensor for measuring the amount or concentration of one or more analytes in a transdermally extracted sample. In one embodiment, the invention includes a sensor element comprising, a sensing electrode that reacts electrochemically with hydrogen peroxide to provide a detectable signal, wherein the sensing electrode comprises a platinum-group metal.

26 Claims, 3 Drawing Sheets

U.S. PATENT DOCUMENTS

| | | | |
|---|---|---|---|
| 5,540,828 A | * | 7/1996 | Yacynych .................. 205/198 |
| 5,636,632 A | | 6/1997 | Rommannan et al. |
| 5,653,918 A | | 8/1997 | Towlson |
| 5,730,714 A | | 3/1998 | Guy et al. |
| 5,735,273 A | | 4/1998 | Kurnik et al. |
| 5,771,890 A | | 6/1998 | Tamada |
| 5,776,372 A | | 7/1998 | Saito et al. |
| 5,795,453 A | | 8/1998 | Gilmartin |
| 5,827,183 A | | 10/1998 | Kurnik et al. |
| 5,928,571 A | | 7/1999 | Chan |
| 5,954,685 A | | 9/1999 | Tierney |
| 5,989,409 A | | 11/1999 | Kurnik et al. |
| 6,042,751 A | | 3/2000 | Chan et al. |
| 6,142,939 A | | 11/2000 | Eppstein et al. |
| 6,309,535 B1 | | 10/2001 | Williams |
| 6,326,160 B1 | | 12/2001 | Dunn et al. |
| 6,391,643 B1 | | 5/2002 | Chen et al. |
| 6,599,408 B1 | | 7/2003 | Chan et al. |

FOREIGN PATENT DOCUMENTS

| | | |
|---|---|---|
| GB | 2 221 300 | 1/1990 |
| GB | 2 335 278 A | 9/1999 |
| WO | WO 89/06989 | 8/1989 |
| WO | WO 95/02357 | 1/1995 |
| WO | WO 96/00109 | 1/1996 |
| WO | WO 96/00110 | 1/1996 |
| WO | WO 97/02811 | 1/1997 |
| WO | WO 97/04832 | 2/1997 |
| WO | WO 97/10356 | 3/1997 |
| WO | WO 97/10499 | 3/1997 |
| WO | WO 97/24059 | 7/1997 |
| WO | WO 98/20331 | 5/1998 |
| WO | WO 98/42252 | 10/1998 |
| WO | WO 99/58050 | 11/1999 |
| WO | WO 99/58051 | 11/1999 |
| WO | WO 99/58190 | 11/1999 |
| WO | WO 99/58973 | 11/1999 |

OTHER PUBLICATIONS

The Diabetes Control and Complications Trial Research, *New Engl. J. Med.* 329:977–986, 1035–1036 (1993).

* cited by examiner

BIOSENSOR, IONTOPHORETIC SAMPLING SYSTEM, AND METHODS OF USE THEREOF

CROSS REFERENCE TO RELATED APPLICATIONS

This application is a continuation of U.S. application Ser. No. 09/267,750, filed Mar. 10, 1999, now U.S. Pat. No. 6,587,705, which is a continuation-in-part of application Ser. No. 09/174,902 filed Oct. 19, 1998, now abandoned, from which applications priority is claimed under 35 USC §120, which are related to provisional patent applications Serial Nos. 60/077,993, filed Mar. 13, 1998, and 60/080,591, filed Apr. 3, 1998, from which applications priority is claimed under 35 USC §119(e)(1), and which applications are incorporated herein by reference in their entireties.

TECHNICAL FIELD

This invention relates generally to a biosensor for use in monitoring the concentration of target chemical analytes present in an aqueous biological system. More particularly, the invention relates to a biosensor for measuring the concentration of one or more analytes in a transdermally extracted sample. The invention also relates to an electrode system for continual transdermal extraction of one or more analytes from a biological system over an extended period of operation. One important application of the invention involves a sampling system for monitoring blood glucose using noninvasive or minimally invasive sampling techniques.

BACKGROUND

A number of diagnostic tests are routinely performed on humans to evaluate the amount or existence of substances present in blood or other body fluids. These diagnostic tests typically rely on physiological fluid samples removed from a subject, either using a syringe or by pricking the skin. One particular diagnostic test entails self-monitoring of blood glucose levels by diabetics.

Diabetes is a major health concern, and treatment of the more severe form of the condition, Type I (insulin-dependent) diabetes, requires one or more insulin injections per day. Insulin controls utilization of glucose or sugar in the blood and prevents hyperglycemia which, if left uncorrected, can lead to ketosis. On the other hand, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise.

Conventional blood glucose monitoring methods generally require the drawing of a blood sample (e.g., by fingerprick) for each test, and a determination of the glucose level using an instrument that reads glucose concentrations by electrochemical or colorimetric methods. Type I diabetics must obtain several fingerprick blood glucose measurements each day in order to maintain tight glycemic control. However, the pain and inconvenience associated with this blood sampling, along with the fear of hypoglycemia, has lead to poor patient compliance, despite strong evidence that tight control dramatically reduces long-term diabetic complications. In fact, these considerations can often lead to an abatement of the monitoring process by the diabetic.

Recently, various methods for determining the concentration of blood analytes without drawing blood have been developed. For example, U.S. Pat. No. 5,267,152 to Yang et al. describes a noninvasive technique of measuring blood glucose concentration using near-IR radiation diffuse-reflection laser spectroscopy. Similar near-IR spectrometric devices are also described in U.S. Pat. No. 5,086,229 to Rosenthal et al. and U.S. Pat. No. 4,975,581 to Robinson et al.

U.S. Pat. No. 5,139,023 to Stanley describes a transdermal blood glucose monitoring apparatus that relies on a permeability enhancer (e.g., a bile salt) to facilitate transdermal movement of glucose along a concentration gradient established between interstitial fluid and a receiving medium. U.S. Pat. No. 5,036,861 to Sembrowich describes a passive glucose monitor that collects perspiration through a skin patch, where a cholinergic agent is used to stimulate perspiration secretion from the eccrine sweat gland. Similar perspiration collection devices are described in U.S. Pat. No. 5,076,273 to Schoendorfer and U.S. Pat. No. 5,140,985 to Schroeder.

In addition, U.S. Pat. No. 5,279,543 to Glikfeld describes the use of iontophoresis to noninvasively sample a substance through skin into a receptacle on the skin surface. Glikfeld suggests that this sampling procedure can be coupled with a glucose-specific biosensor or glucose-specific electrodes in order to monitor blood glucose. Finally, International Publication No. WO 96/00110 to Tamada describes an iontophoretic apparatus for transdermal monitoring of a target substance, where an iontophoretic electrode is used to move an analyte into a collection reservoir and a biosensor is used to detect the target analyte present in the reservoir.

However, there remains a need in the art for sampling devices and sampling methods which provide low cost, accurate determination of analyte concentrations in field or home-testing applications, particularly where continual and/or automatic monitoring is desired.

SUMMARY OF THE INVENTION

Accordingly, the present invention provides an efficient sampling system for detecting and/or measuring the concentration of a transdermally extracted analyte. The invention represents an improvement over prior noninvasive monitoring techniques and devices by providing an automatic sampling system coupled with a highly sensitive biosensor for determining the concentration of a target analyte present in an aqueous biological system. The sampling system extracts small amounts of a target analyte via transdermal methods, and then senses and/or quantifies the concentration of the target analyte. Sampling is carried out in a continual manner, allowing quantification to be carried out even when a target analyte, extracted from the biological system, is obtained at a sub-millimolar (sub-mM) concentration.

The advantages provided by the invention are thus several fold. For example, the noninvasive nature of the sampling system significantly increases the likelihood of patient acceptance. In the particular context of blood glucose monitoring, better glycemic control can be achieved by taking frequent blood glucose measurements on a daily basis, and using that information to determine the amount and frequency of insulin administration. Use of the noninvasive sampling system of the invention helps increase the likelihood that such frequent measurements will be taken. In addition, the automatic sampling provided by the instant sampling system, particularly when taken over an extended period of time (e.g., 24 hours or more) can be used to monitor concentration swings previously not detectable using prior devices. Again in the context of blood glucose monitoring, it is now believed that even four to seven glucose measurements per day may be insufficient to reflect the diurnal glucose level variation in many diabetics. Using the instant sampling system to automatically measure blood glucose at, for example, a frequency of once per hour, allows monitoring of previously unrecognizable glucose swings, particularly when a subject is asleep. Thus, the invention provides access to information that is of great clinical benefit in home, field and/or medical environments.

Accordingly, it is a general object of the invention to provide an automated system for continual transdermal extraction of analytes present in biological fluids. In one particular embodiment, the transdermal extraction is carried out using reverse iontophoresis or electroosmosis to extract analytes across a subject's skin. In this embodiment, one or more collection reservoirs are contacted with a subject's skin. The reservoirs typically contain a conductive medium and are in contact with a sampling means for providing electric potential or current between the reservoir site and another site on the subject's skin. A biosensor is also in contact with the one or more reservoirs, and provides a means for sensing and/or quantifying the concentration of a target analyte present in the reservoirs.

In a preferred embodiment, an automated system for iontophoretic extraction of analytes is provided, wherein iontophoretic electrodes capable of continual cycling under iontophoretic conditions are used to transdermally extract analytes continually over a period of about 1–24 hours, or longer. Therefore, unlike most iontophoresis applications, the iontophoretic electrodes of the invention are capable of passing current in both directions without concomitantly participating in undesirable side reactions, particularly water hydrolysis. In addition, the electrodes must have the capacity to pass a high amount of charge, which capacity is readily reversible so that the electrodes pass current reproducibly for an extended period of operation.

In another embodiment, an automated system for continual transdermal extraction of analytes present in biological fluids is provided, wherein the transdermal extraction is carried out using sonophoresis to extract analytes across a subject's skin. In this embodiment, a collection reservoir is contacted with a subject's skin. The reservoir contains a conductive medium, and is in contact with a sampling means for applying ultrasound to the contacted skin surface such that noninvasive sampling of analytes beneath the skin surface can be carried out. A biosensor is also in contact with the reservoir, providing a means for sensing and/or quantifying the concentration of a target analyte extracted into the reservoir.

In each of the iontophoretic and sonophoretic sampling systems of the invention, the collection reservoirs are comprised of a liquid, or liquid-containing medium which is ionically conductive and efficiently transmits the electric potential or current, or the ultrasound, between the respective sampling means and the skin surface. In preferred embodiments, the liquid-containing medium is an ionically conductive hydrogel or wicking material soaked with an ionically conductive medium.

As will be understood by the ordinarily skilled artisan upon reading the present specification, there are a large number of analytes that can be sampled using the present automated sampling systems. In systems which rely on the reverse iontophoresis/electroosmosis techniques described herein, charged (e.g., having a negative or positive ionic charge) substances will be extracted at the highest concentrations, while uncharged substances will be extracted at lower, albeit still quantifiable, concentrations. One particular uncharged analyte of interest herein is glucose. Other analytes of interest include, but are not limited to, amino acids, enzyme substrates or products indicative of a disease state or condition, therapeutic agents, drugs of abuse, and electrolytes.

The biosensor used for sensing and/or quantitating the target analyte extracted by the present sampling system needs to perform reliably and reproducibly using extracted concentrations (e.g., sub-mM) which are well below those measured by conventional electrochemical detection (generally in the mM range). As used herein, "sub-mM" refers to and concentration that is less than 1 mM. In one particular embodiment, the biosensor includes an electrode comprising a platinum-group metal (e.g., Pt, Pd, Ru, and Rh). The biosensor electrode is used to detect hydrogen peroxide generated by an enzyme oxidase which specifically reacts with an analyte of interest to provide hydrogen peroxide. Since the automatic sampling system is used to provide continual or periodic sampling over an extended period of operation, the biosensor electrode must have a low background current, and be stable for at least about 1–24 hours of operation. The biosensor electrode further must have high sensitivity for the hydrogen peroxide signal, where a preferred sensitivity (nA/$\mu$M): background current (nA) ratio is on the order of about 3 or greater. Finally, the biosensor electrode must exhibit reduced catalytic peroxide decomposition by the platinum-group metal constituent.

Accordingly, it is a primary object of the invention to provide sampling system for monitoring the concentration of an analyte present in a biological system. The sampling system comprises:

(a) a reservoir containing an ionically conductive medium and an enzyme capable of reacting with the analyte to produce hydrogen peroxide;

(b) sampling means in operative contact with the reservoir, wherein the sampling means is used for extracting the analyte from the biological system into the reservoir to obtain a sub-millimolar (sub-mM) concentration of the analyte in the reservoir which reacts with the enzyme to produce hydrogen peroxide; and (c) a sensor element also in operative contact with the reservoir, wherein the sensor element reacts electrochemically with the hydrogen peroxide produced in the reservoir to provide a detectable signal. The sensor element comprises an electrode having suitable geometric surface area and background noise so as to be effective in the present sampling system.

It is also a primary object of the invention to provide a sampling system for monitoring the concentration of an analyte present in a biological system, wherein the sampling system comprises:

(a) a reservoir containing an ionically conductive medium and an enzyme capable of reacting with the analyte to produce hydrogen peroxide;

(b) reverse iontophoretic sampling means in operative contact with the reservoir, wherein the reverse iontophoretic sampling means is used for extracting the analyte from the biological system into the reservoir to obtain a sub-millimolar (sub-mM) concentration of the analyte in the reservoir which reacts with the enzyme to produce hydrogen peroxide; and (c) a sensor element also in operative contact with the reservoir, wherein the sensor element reacts electrochemically with the hydrogen peroxide produced in the reservoir to provide a detectable signal. The reverse iontophoretic sampling means comprises first and second iontophoretic electrodes having suitable geometric area and current carrying capability so as to be operative in the present sampling system.

It is a still further object of the invention to provide a method for monitoring the concentration of an analyte present in a biological system, wherein the method comprises the following steps:

(a) extracting an analyte from the biological system into a collection reservoir to provide a sub-millimolar (sub-mM) concentration of the analyte in the reservoir;

(b) contacting the analyte extracted in step (a) with an enzyme that reacts with the analyte to produce hydrogen peroxide;

(c) detecting the hydrogen peroxide produced in step (b) with a sensor element, wherein the sensor element reacts electrochemically with the hydrogen peroxide to produce a detectable signal;

(d) measuring the signal produced in step (c);

(e) correlating the measurement obtained in step (d) with the concentration of the analyte in the biological system; and (f) performing steps (a)–(d) continually or periodically over an extended period of operation. The sensor element comprises an electrode having suitable geometric surface area and background noise so as to be operative in the present method. Optionally, the method can be carried out using a reverse iontophoretic system to transdermally extract the analyte from the biological system, wherein the iontophoretic electrodes have suitable geometric area and current carrying capability so as to be operative in the present method.

In a further aspect of the above embodiments, the sensor element can also include a reference electrode, and a counter electrode. Further, a counter electrode of the sensor element and an iontophoretic electrode of the sampling system can be combined as a single bimodal electrode where the electrode is not used simultaneously for both functions, i.e., where the counter and iontophoretic functions are separately carried out at different times.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

Figure 1:
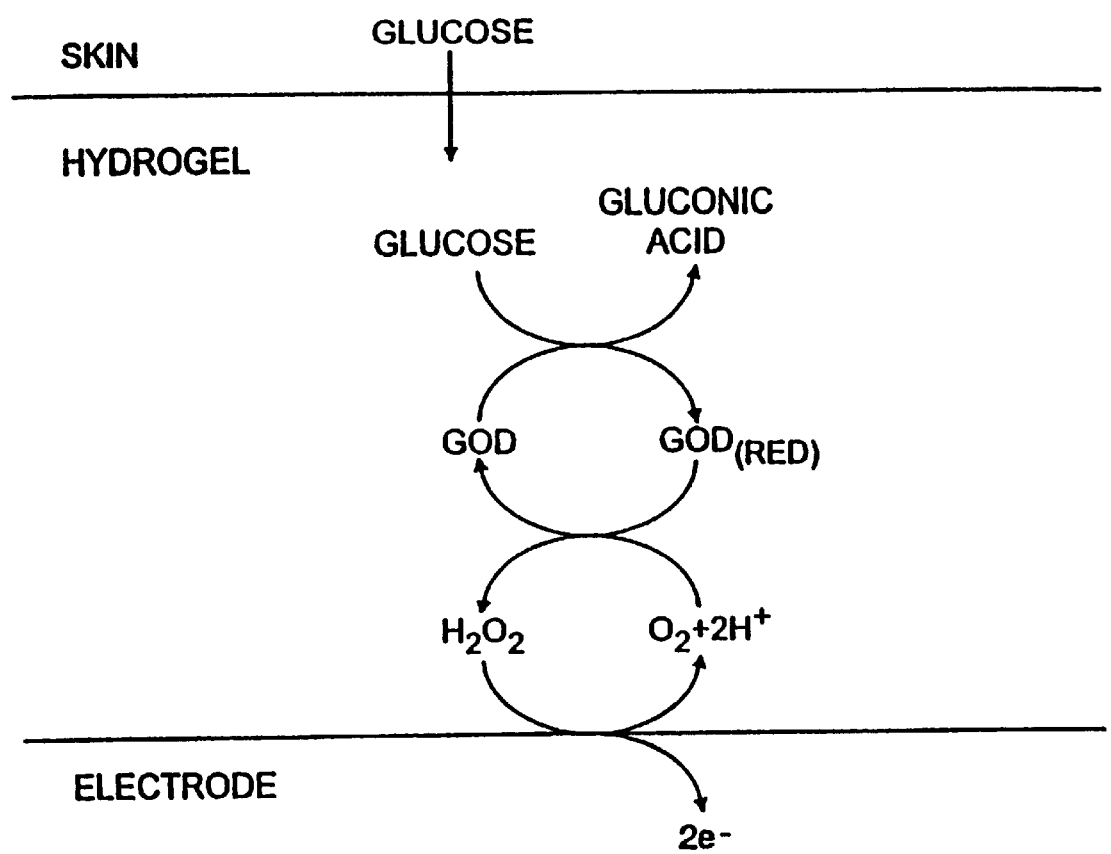
FIG. 1 is a schematic representation of the reaction which glucose oxidase (GOx) catalyzes to obtain gluconic acid and hydrogen peroxide, and result in the generation of a current.

Before describing the present invention in detail, it is to be understood that this invention is not limited to particular compositions or biological systems as such may, of course, vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the content clearly dictates otherwise. Thus, for example, reference to "a binder" includes a mixture of two or more such binders, reference to "an analyte" includes mixtures of analytes, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

In describing and claiming the present invention, the following terminology will be used in accordance with the definitions set out below.

The terms "analyte" and "target analyte" are used herein to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte. Furthermore, the terms "analyte" and "substance" are used interchangeably herein, and are intended to have the same meaning, and thus encompass any substance of interest. In preferred embodiments, the physiological analyte of interest is, for example, glucose, or a chemical that has a physiological action, for example a drug or pharmacological agent.

A "sampling device" or "sampling system" refers to any device for obtaining a sample from a biological system for the purpose of determining the concentration of an analyte of interest. As used herein, the term "sampling" means invasive, minimally invasive or non-invasive extraction of a substance from the biological system, generally across a membrane such as skin or mucosa. The membrane can be natural or artificial, and can be of plant or animal nature, such as natural or artificial skin, blood vessel tissue, intestinal tissue, and the like. Typically, the sampling means are in operative contact with a "reservoir," wherein the sampling means is used for extracting the analyte from the biological system into the reservoir to obtain the analyte in the reservoir. A "biological system" includes both living and artificially maintained systems. Examples of minimally invasive and noninvasive sampling techniques include iontophoresis, sonophoresis, suction, electroporation, thermal poration, passive diffusion, microfine (miniature) lances or cannulas, subcutaneous implants or insertions, and laser devices. Sonophoresis uses ultrasound to increase the permeability of the skin (see, e.g., Menon et al. (1994) *Skin Pharmacology* 7:130–139). Suitable sonophoresis sampling systems are described in International Publication No. WO 91/12772, published Sep. 5, 1991. Passive diffusion sampling devices are described, for example, in International Publication Nos.: WO 97/38126 (published Oct. 16, 1997); WO 97/42888, WO 97/42886, WO 97/42885, and WO 97/42882 (all published Nov. 20, 1997); and WO 97/43962 (published Nov. 27, 1997). Laser devices use a small laser beam to burn a hole through the upper layer of the patient's skin (see, e.g., Jacques et al. (1978) *J. Invest. Dermatology* 88:88–93). Examples of invasive sampling techniques include traditional needle and syringe or vacuum sample tube devices.

A "monitoring system," as used herein, refers to a system useful for continually or continuously measuring a physiological analyte present in a biological system. Such a system typically includes, but is not limited to, sampling means, sensing means, and a microprocessor means in operative communication with the sampling means and the sensing means.

The term "artificial," as used herein, refers to an aggregation of cells of monolayer thickness or greater which are grown or cultured in vivo or in vitro, and which function as a tissue of an organism but are not actually derived, or excised, from a pre-existing source or host.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term "continual measurement" intends a series of two or more measurements obtained from a particular biological system, which measurements are obtained using a single device maintained in operative contact with the biological system over the time period in which the series of measurements is obtained. The term thus includes continuous measurements.

The term "transdermal," as used herein, includes both transdermal and transmucosal techniques, i.e., extraction of a target analyte across skin or mucosal tissue. Aspects of the invention which are described herein in the context of "transdermal," unless otherwise specified, are meant to apply to both transdermal and transmucosal techniques.

The term "transdermal extraction," or "transdermally extracted" intends any noninvasive, or at least minimally invasive sampling method, which entails extracting and/or transporting an analyte from beneath a tissue surface across skin or mucosal tissue. The term thus includes extraction of an analyte using iontophoresis (reverse iontophoresis), electroosmosis, sonophoresis, microdialysis, suction, and passive diffusion. These methods can, of course, be coupled with application of skin penetration enhancers or skin permeability enhancing technique such as tape stripping or pricking with micro-needles. The term "transdermally extracted" also encompasses extraction techniques which employ thermal poration, electroporation, microfine lances, microfine canulas, subcutaneous implants or insertions, and the like.

The term "iontophoresis" intends a method for transporting substances across tissue by way of an application of electrical energy to the tissue. In conventional iontophoresis, a reservoir is provided at the tissue surface to serve as a container of material to be transported. Iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode).

The term "reverse iontophoresis" refers to the movement of a substance from a biological fluid across a membrane by way of an applied electric potential or current. In reverse iontophoresis, a reservoir is provided at the tissue surface to receive the extracted material.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device," "sensing means," or "biosensor device" encompasses any device that can be used to measure the concentration of an analyte, or derivative thereof, of interest. Preferred sensing devices for detecting blood analytes generally include electrochemical devices and chemical devices. Examples of electrochemical devices include the Clark electrode system (see, e.g., Updike et al. (1967) *Nature* 214:986–988) and other amperometric, coulometric, or potentiometric electrochemical devices. Examples of chemical devices include conventional enzyme-based reactions as used in the Lifescan® glucose monitor (Johnson and Johnson, New Brunswick, N.J.) (see, e.g., U.S. Pat. No. 4,935,346 to Phillips et al.).

A "biosensor" or "biosensor device" includes, but is not limited to, a "sensor element" which includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface which converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (*Analytical Chemistry* 67(24), 4594–4599, 1995).

The "sensor element" can include components in addition to a biosensor electrode, for example, it can include a "reference electrode," and a "counter electrode." The term "reference electrode" is used herein to mean an electrode that provides a reference potential, e.g., a potential can be established between a reference electrode and a working electrode. The term "counter electrode" is used herein to mean an electrode in an electrochemical circuit which acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are most preferred.

In one embodiment, the "counter electrode" of the "sensor element" comprises a "bimodal electrode." The term "bimodal electrode" as used herein typically refers to an electrode which is capable of functioning non-simultaneously as, for example, both the counter electrode (of the "sensor element") and the iontophoretic electrode (of the "sampling means").

The terms "reactive surface," and "reactive face" are used interchangeably herein to mean the surface of the sensing electrode that: (1) is in contact with the surface of an electrolyte containing material (e.g. gel) which contains an analyte or through which an analyte, or a derivative thereof, flows from a source thereof; (2) is comprised of a catalytic material (e.g., carbon, platinum, palladium, rhodium, ruthenium, or nickel and/or oxides, dioxides and combinations or alloys thereof) or a material that provides sites for electrochemical reaction; (3) converts a chemical signal (e.g. hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal that is correlatable with the amount of analyte present in the electrolyte.

The term "collection reservoir" is used to describe any suitable containment means for containing a sample extracted from a biological system. The reservoir can include a material which is ionically conductive (e.g., water with ions therein), wherein another material such as a sponge-like material or hydrophilic polymer is used to keep the water in place. Such collection reservoirs can be in the form of a hydrogel (for example, in the shape of a disk or pad). Other suitable collection reservoirs include, but are not limited to, tubes, vials, capillary collection devices, cannulas, and miniaturized etched, ablated or molded flow paths.

An "ionically conductive material" refers to any material that provides ionic conductivity, and through which electrochemically active species can diffuse. The ionically conductive material can be, for example, a solid, liquid, or semisolid (e.g., in the form of a gel) material that contains an electrolyte, which can be composed primarily of water and ions (e.g., sodium chloride), and generally comprises 50% or more water by weight. The material can be in the form of a gel, a sponge or pad (e.g., soaked with an electrolytic solution), or any other material that can contain an electrolyte and allow passage therethrough of electrochemically active species, especially the analyte of interest.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

By the term "printed" as used herein is meant a substantially uniform deposition of an electrode formulation onto one surface of a substrate (i.e., the base support). It will be appreciated by those skilled in the art that a variety of techniques may be used to effect substantially uniform deposition of a material onto a substrate, e.g., Gravure-type printing, extrusion coating, screen coating, spraying, painting, or the like.

General Methods

A method and apparatus for sampling small amounts of an analyte via transdermal methods are provided. The method and apparatus are used to detect and/or quantify the concentration of a target analyte present in a biological system. This sampling is carried out in a continual manner, and quantification is possible even when the target analyte is extracted sample in sub-millimolar concentrations. Although the method and apparatus are broadly applicable to sampling any chemical analyte and/or substance, the invention is expressly exemplified for use in transdermal sampling and quantifying or qualifying glucose or a glucose metabolite.

Accordingly, in one aspect of the method of the invention, an automatic sampling system is used to monitor levels of glucose in a biological system. The method can be practiced using a sampling system (device) which transdermally extracts glucose from the system, in this case, an animal subject. Transdermal extraction is carried out by applying an electrical current or ultrasonic radiation to a tissue surface at a collection site. The electrical current or ultrasonic radiation is used to extract small amounts of glucose from the subject into a collection reservoir. The collection reservoir is in contact with a biosensor which provides for measurement of glucose concentration in the subject.

In the practice of the method, a collection reservoir is contacted with a tissue surface, for example, on the stratum corneum of a patient's skin. An electrical or ultrasonic force is then applied to the tissue surface in order to extract glucose from the tissue into the collection reservoir. Extraction is carried out continually over a period of about 1–24 hours, or longer. The collection reservoir is analyzed, at least periodically, to measure glucose concentration therein. The measured value correlates with the subject's blood glucose level.

More particularly, one or more collection reservoirs are placed in contact with a tissue surface on a subject. The collection reservoirs are also contacted with an electrode which generates a current (for reverse iontophoretic extraction) or with a source of ultrasonic radiation such as a transducer (for sonophoretic extraction) sufficient to extract glucose from the tissue into the collection reservoir.

The collection reservoir contains an ionically conductive liquid or liquid-containing medium. The conductive medium is preferably a hydrogel which can contain ionic substances in an amount sufficient to produce high ionic conductivity. The hydrogel is formed from a solid material (solute) which, when combined with water, forms a gel by the formation of a structure which holds water including interconnected cells and/or network structure formed by the solute. The solute may be a naturally occurring material such as the solute of natural gelatin which includes a mixture of proteins obtained by the hydrolysis of collagen by boiling skin, ligaments, tendons and the like. However, the solute or gel forming material is more preferably a polymer material (including, but not limited to, polyethylene oxide, polyvinyl alcohol, polyacrylic acid, polyacrylamidomethylpropanesulfonate and copolymers thereof, and polyvinyl pyrrolidone) present in an amount in the range of more than 0.5% and less than 40% by weight, preferably 8 to 12% by weight when a humectant is also added, and preferably about 15 to 20% by weight when no humectant is added. Additional materials may be added to the hydrogel, including, without limitation, electrolyte (e.g., a salt), buffer, tackifier, humectant, biocides, preservatives and enzyme stabilizers. Suitable hydrogel formulations are described in International Publication Nos. WO 97/02811, published Jan. 30, 1997, and WO 96/00110, published Jan. 4, 1996, each of which publications are incorporated herein by reference in their entireties.

Since the sampling system of the present invention must be operated at very low (electrochemical) background noise levels, the collection reservoir must contain an ionically conductive medium that does not include significant electrochemically sensitive components and/or contaminants. Thus, the preferred hydrogel composition described hereinabove is formulated using a judicious selection of materials and reagents which do not add significant amounts of electrochemical contaminants to the final composition.

In order to facilitate detection of the analyte, an enzyme is disposed within the one or more collection reservoirs. The enzyme is capable of catalyzing a reaction with the extracted analyte (in this case glucose) to the extent that a product of this reaction can be sensed, e.g., can be detected electrochemically from the generation of a current which current is detectable and proportional to the amount of the analyte which is reacted. A suitable enzyme is glucose oxidase which oxidizes glucose to gluconic acid and hydrogen peroxide. The subsequent detection of hydrogen peroxide on an appropriate biosensor electrode generates two electrons per hydrogen peroxide molecule which create a current which can be detected and related to the amount of glucose entering the device (see FIG. 1). Glucose oxidase (GOx) is readily available commercially and has well known catalytic characteristics. However, other enzymes can also be used, so long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

The biosensor electrode must be able to detect the glucose analyte extracted into the one or more collection reservoirs even when present at nominal concentration levels. In this regard, conventional electrochemical detection systems which utilize glucose oxidase (GOx) to specifically convert glucose to hydrogen peroxide, and then detect with an appropriate electrode, are only capable of detecting the analyte when present in a sample in at least mM concentrations. In contrast, the present invention allows sampling and detection of small amounts of analyte from the subject, wherein the analyte is detected at concentrations on the order of 2 to 4 orders of magnitude lower (e.g., $\mu$M concentration in the reservoir) than presently detectable with conventional systems.

Accordingly, the biosensor electrode of the present invention must exhibit substantially reduced background current relative to prior such electrodes. In one particularly preferred embodiment, an electrode is provided which contains platinum (Pt) and graphite dispersed within a polymer matrix. The electrode exhibits the following features, each of which are essential to the effective operation of the biosensor: background current in the electrode due to changes in the Pt oxidation state and electrochemically sensitive contaminants in the electrode formulation is substantially reduced; and catalytic activity (e.g., nonelectrochemical hydrogen peroxide decomposition) by the Pt in the electrode is reduced.

The Pt-containing electrode is configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode is specially formulated to provide a high signal-to-noise ratio (S/N ratio) for this geometric surface area not heretofore available with prior Pt-containing electrodes. For example, a Pt-containing electrode constructed according to the invention and having a geometric area of about 1 $cm^2$ preferably has a background current on the order of about 20 nA or less (when measured with buffer solution at 0.6V), and has high sensitivity (e.g., at least about 60 nA/$\mu$M of $H_2O_2$ in buffer at 0.6V). In like manner, an electrode having a geometric area of about 0.1 $cm^2$ preferably has a background current of about 2 nA or less and sensitivity of at least about 6 nA/$\mu$M of $H_2O_2$; and an electrode having a geometric area of about 3 $cm^2$ preferably has a background current of about 60 nA or less and sensitivity of at least about 180 nA/$\mu$M of $H_2O_2$, both as measured in buffer at 0.6V. These features provide for a high S/N ratio, for example a S/N ratio of about 3 or greater. The electrode composition is formulated using analytical- or electronic-grade reagents and solvents which ensure that electrochemical and/or other residual contaminants are avoided in the final composition, significantly reducing the background noise inherent in the resultant electrode. In particular, the reagents and solvents used in the formulation of the electrode are selected so as to be substantially free of electrochemically active contaminants (e.g., anti-oxidants), and the solvents in particular are selected for high volatility in order to reduce washing and cure times.

The Pt powder used to formulate the electrode composition is also substantially free from impurities, and the Pt/graphite powders are evenly distributed within the polymer matrix using, for example, co-milling or sequential milling of the Pt and graphite. Alternatively, prior to incorporation into the polymer matrix, the Pt can be sputtered onto the graphite powder, colloidal Pt can be precipitated onto the graphite powder (see, e.g., U.K. patent application number GB 2,221,300, published Jan. 31, 1990, and references cited therein), or the Pt can be adsorbed onto the graphite powder to provide an even distribution of Pt in contact with the conductive graphite. In order to improve the S/N ratio of the electrode, the Pt content in the electrode is lower relative to prior Pt or Pt-based electrodes. In a preferred embodiment, the overall Pt content is about 3–7% by weight. Although decreasing the overall amount of Pt may reduce the sensitivity of the electrode, the inventors have found that an even greater reduction in background noise is also achieved, resulting in a net improvement in signal-to-noise quality.

The Pt/graphite matrix is supported by a suitable binder, such as an electrochemically inert polymer or resin binder, which is selected for good adhesion and suitable coating integrity. The binder is also selected for high purity, and for absence of components with electrochemical background. In this manner, no electrochemically sensitive contaminants are introduced into the electrode composition by way of the binder. A large number of suitable such binders are known in the art and are commercially available, including, without limitation, vinyl, acrylic, epoxy, phenoxy and polyester polymers, provided that the binder or binders selected for the formulation are adequately free of electroactive impurities.

The Pt/graphite biosensor electrodes formulated above exhibit reduced catalytic activity (e.g., passive or nonelectrochemical hydrogen peroxide degradation) relative to prior Pt-based electrode systems, and thus have substantially improved signal-to-noise quality. In preferred Pt/graphite electrode compositions, the biosensor exhibits about 10–25% passive hydrogen peroxide degradation as measured in the assay of Example 2, infra, preferably less than about 20% passive degradation.

Once formulated, the electrode composition is affixed to a suitable nonconductive surface which may be any rigid or flexible material having appropriate insulating and/or dielectric properties. The electrode composition can be affixed to the surface in any suitable pattern or geometry, and can be applied using various thin film techniques, such as sputtering, evaporation, vapor phase deposition, or the like; or using various thick film techniques, such as film laminating, electroplating, or the like. Alternatively, the composition can be applied using screen printing, pad printing, inkjet methods, transfer roll printing, or similar techniques. Preferably, the electrode is applied using a low temperature screen print onto a polymeric substrate. The screening can be carried out using a suitable mesh, ranging from about 100–400 mesh.

As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (for example, employing an algorithm using statistical methods) by an associated system controller to provide a glucose concentration value for display.

In one embodiment of the present invention, the sampling system can have two collection reservoirs which contain, for example, an active collection reservoir, having the GOx enzyme, and a blank collection reservoir (without the GOx enzyme); or, in an alternative, two active reservoirs, i.e., two reservoirs containing the GOx enzyme. In the case of an active collection reservoir and a blank collection reservoir signal can be adjusted by subtraction of the blank reservoir signal from the signal obtained from the active reservoir. In the case of two active collection reservoirs the signals can be summed and averaged, or a total of the two signals can be used. This signal, for example the detected current, is then used alone or in combination with other factors (for example, glucose concentration at a calibration point, skin temperature, conductivity, voltage, time since calibration of the system, etc.) to provide a glucose concentration value.

In particular embodiments, the detected current can be correlated with the subject's blood glucose concentration (typically using statistical algorithms associated with a microprocessor) so that the system controller may display the subject's actual blood glucose concentration as measured by the sampling system. For example, the system can be calibrated to the subject's actual blood glucose concentration by sampling the subject's blood during a standard glucose tolerance test, and analyzing the blood glucose using both a standard blood glucose monitor and the sampling system of the present invention. In addition or alternately, the sampling system can be calibrated at a calibration time point where the signal obtained from the sampling system at that time point is correlated to blood glucose concentration at that time point as determined by direct blood testing (for example, glucose concentration can be determined using a HemoCue® clinical analyzer (HemoCue AB, Sweden)). In this manner, measurements obtained by the sampling system can be correlated to actual values using known statistical techniques. Such statistical techniques can be formulated as algorithm(s) and incorporated in a microprocessor associated with the sampling system.

Further, the sampling system can be pre-programmed to begin execution of its signal measurements (or other functions) at a designated time. One application of this feature is to have the sampling system in contact with a subject and to program the sampling system to begin sequence execution during the night so that it is available for calibration immediately upon waking. One advantage of this feature is that it removes any need to wait for the sampling system to warm-up before calibrating it.

In one preferred embodiment, the automatic sampling system transdermally extracts the sample in a continual manner over the course of a 1–24 hour period, or longer, using reverse iontophoresis. More particularly, the collection reservoir contains an ionically conductive medium, preferably the hydrogel medium described hereinabove. A first iontophoresis electrode is contacted with the collection reservoir (which is in contact with a target tissue surface), and a second iontophoresis electrode is contacted with either a second collection reservoir in contact with the tissue surface, or some other ionically conductive medium in contact with the tissue. A power source provides an electric potential between the two electrodes to perform reverse iontophoresis in a manner known in the art. As discussed above, the biosensor selected to detect the presence, and possibly the level, of the target analyte (glucose) within a reservoir is also in contact with the reservoir.

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in International Publication No. WO 96/00110, published Jan. 4, 1996.

As an example, to extract glucose, the applied electrical current density on the skin or tissue is preferably in the range of about 0.01 to about 2 $mA/cm^2$. In a preferred embodiment, in order to facilitate the extraction of glucose, electrical energy is applied to the electrodes, and the polarity of the electrodes is alternated at a rate of about one switch every 7.5 minutes (for a 15 minute extraction period), so that each electrode is alternately a cathode or an anode. The polarity switching can be manual or automatic.

Any suitable iontophoretic electrode system can be employed, however it is preferred that a silver/silver chloride (Ag/AgCl) electrode system is used. The iontophoretic electrodes are formulated using two critical performance parameters: (1) the electrodes are capable of continual operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes.

Figure 3:
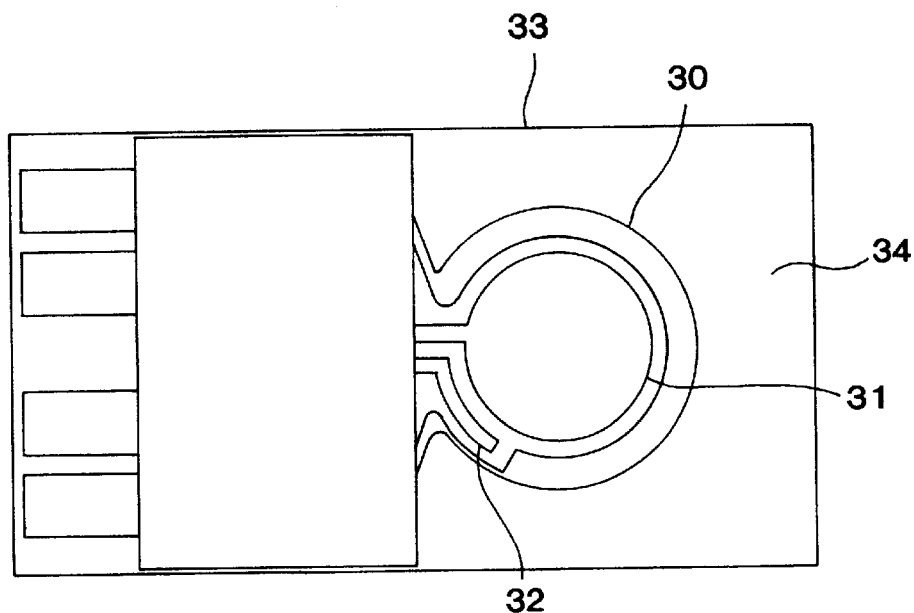
FIG. 3 is a representation of one embodiment of a bimodal electrode design. The figure presents an overhead and schematic view of the electrode assembly 33. In the figure, the bimodal electrode is shown at 30 and can be, for example, a Ag/AgCl iontophoretic/counter electrode. The sensing or working electrode (made from, for example, platinum) is shown at 31. The reference electrode is shown at 32 and can be, for example, a Ag/AgCl electrode. The components are mounted on a suitable substance 34. In this example of such an electrode the working electrode area is approximately 1.35 cm$^2$.
Figure 4:
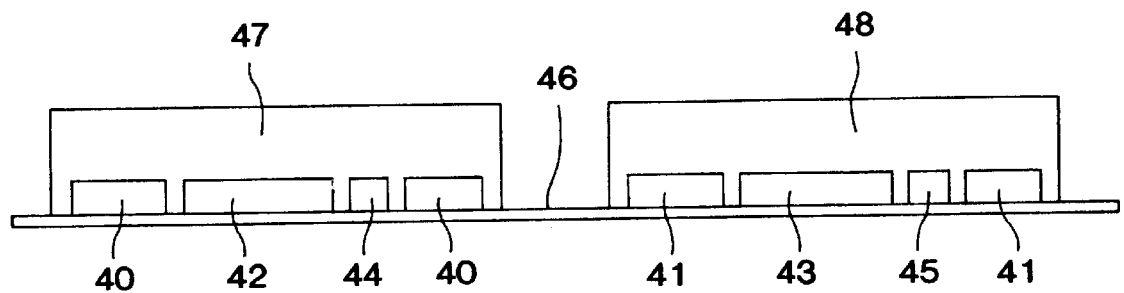
FIG. 4 is a representation of a cross-sectional schematic view of the bimodal electrodes as they may be used in conjunction with a reference electrode and a hydrogel patch. In the figure, the components are as follows: bimodal electrodes 40 and 41; sensing electrodes 42 and 43; reference electrodes 44 and 45; a substrate 46; and hydrogel pads 47 and 48.

In an alternative embodiment, the sampling device can operate in an alternating polarity mode necessitating the presence of a first and second bimodal electrodes (FIG. 4, 40 and 41) and two collection reservoirs (FIG. 4, 47 and 48). In the present invention, each bi-modal electrode (FIG. 3, 30; FIG. 4, 40 and 41) serves two functions depending on the phase of the operation: (1) an electro-osmotic electrode (or iontophoretic electrode) used to electrically draw analyte from a source into a collection reservoir comprising water and an electrolyte, and to the area of the electrode subassembly; and (2) as a counter electrode to the first sensing electrode at which the chemical compound is catalytically converted at the face of the sensing electrode to produce an electrical signal.

The reference (FIG. 4, 44 and 45; FIG. 3, 32) and sensing electrodes (FIG. 4, 42 and 43; FIG. 3, 31), as well as, the bimodal electrode (FIG. 4, 40 and 41; FIG. 3, 30) are connected to a standard potentiostat circuit during sensing. In general, practical limitations of the system require that the bimodal electrode will not act as both a counter and iontophoretic electrode simultaneously.

The general operation of an iontophoretic sampling system is the cyclical repetition of two phases: (1) a reverse-iontophoretic phase, followed by a (2) sensing phase. During the reverse iontophoretic phase, the first bimodal electrode (FIG. 4, 40) acts as an iontophoretic cathode and the second bimodal electrode (FIG. 4, 41) acts as an iontophoretic anode to complete the circuit. Analyte is collected in the reservoirs, for example, a hydrogel (FIG. 4, 47 and 48). At the end of the reverse iontophoretic phase, the iontophoretic current is turned off. During the sensing phase, in the case of glucose, a potential is applied between the reference electrode (FIG. 4, 44) and the sensing electrode (FIG. 4, 42). The chemical signal reacts catalytically on the catalytic face of the first sensing electrode (FIG. 4, 42) producing an electrical current, while the first bi-modal electrode (FIG. 4, 40) acts as a counter electrode to complete the electrical circuit.

The electrode described is particularly adapted for use in conjunction with a hydrogel collection reservoir system for monitoring glucose levels in a subject through the reaction of collected glucose with the enzyme glucose oxidase present in the hydrogel matrix.

The bi-modal electrode is preferably comprised of Ag/AgCl. The electrochemical reaction which occurs at the surface of this electrode serves as a facile source or sink for electrical current. This property is especially important for the iontophoresis function of the electrode. Lacking this reaction, the iontophoresis current could cause the hydrolysis of water to occur at the iontophoresis electrodes causing pH changes and possible gas bubble formation. The pH changes to acidic or basic pH could cause skin irritation or burns. The ability of an Ag/AgCl electrode to easily act as a source of sink current is also an advantage for its counter electrode function. For a three electrode electrochemical cell to function properly, the current generation capacity of the counter electrode must not limit the speed of the reaction at the sensing electrode. In the case of a large sensing electrode, the ability of the counter electrode to source proportionately larger currents is required.

The design of the present invention provides for a larger sensing electrode (see for example, FIG. 3) than previously designed. Consequently, the size of the bimodal electrode must be sufficient so that when acting as a counter electrode with respect to the sensing electrode the counter electrode does not become limiting the rate of catalytic reaction at the sensing electrode catalytic surface.

Two methods exist to ensure that the counter electrode does not limit the current at the sensing electrode: (1) the bi-modal electrode is made much larger than the sensing electrode, or (2) a facile counter reaction is provided.

During the reverse iontophoretic phase, the power source provides a current flow to the first bi-modal electrode to facilitate the extraction of the chemical signal into the reservoir. During the sensing phase, the power source is used to provide voltage to the first sensing electrode to drive the conversion of chemical signal retained in reservoir to electrical signal at the catalytic face of the sensing electrode. The power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode sub-assembly can be operated by electrically connecting the bimodal electrodes such that each electrode is capable of functioning as both an iontophoretic electrode and counter electrode along with appropriate sensing electrode(s) and reference electrode(s), to create standard potentiostat circuitry.

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal.

With regard to continual operation for extended periods of time, Ag/AgCl electrodes are provided herein which are capable of repeatedly forming a reversible couple which operates without unwanted electrochemical side reactions (which could give rise to changes in pH, and liberation of hydrogen and oxygen due to water hydrolysis). The Ag/AgCl electrodes of the present invention are thus formulated to withstand repeated cycles of current passage in the range of about 0.01 to 1.0 mA per $cm^2$ of electrode area. With regard to high electrochemical purity, the Ag/AgCl components are dispersed within a suitable polymer binder to provide an electrode composition which is not susceptible to attack (e.g., plasticization) by components in the collection reservoir, e.g., the hydrogel composition. The electrode compositions are also formulated using analytical- or electronic-grade reagents and solvents, and the polymer binder composition is selected to be free of electrochemically active contaminants which could diffuse to the biosensor to produce a background current.

Since the Ag/AgCl iontophoretic electrodes must be capable of continual cycling over extended periods of time, the absolute amounts of Ag and AgCl available in the electrodes, and the overall Ag/AgCl availability ratio, can be adjusted to provide for the passage of high amounts of charge. Although not limiting in the present invention, the Ag/AgCl ratio can approach unity. In order to operate within the preferred system which uses a biosensor having a geometric area of 0.1 to 3 $cm^2$, the iontophoretic electrodes are configured to provide an approximate electrode area of 0.3 to 1.0 $cm^2$, preferably about 0.85 $cm^2$. These electrodes provide for reproducible, repeated cycles of charge passage at current densities ranging from about 0.01 to 1.0 mA/cm² of electrode area. More particularly, electrodes constructed according to the above formulation parameters, and having an approximate electrode area of 0.85 cm², are capable of a reproducible total charge passage (in both anodic and cathodic directions) of 270 mC, at a current of about 0.3 mA (current density of 0.35 mA/cm²) for 48 cycles in a 24 hour period.

Once formulated, the Ag/AgCl electrode composition is affixed to a suitable rigid or flexible nonconductive surface as described above with respect to the biosensor electrode composition. A silver (Ag) underlayer is first applied to the surface in order to provide uniform conduction. The Ag/AgCl electrode composition is then applied over the Ag underlayer in any suitable pattern or geometry using various thin film techniques, such as sputtering, evaporation, vapor phase deposition, or the like, or using various thick film techniques, such as film laminating, electroplating, or the like. Alternatively, the Ag/AgCl composition can be applied using screen printing, pad printing, inkjet methods, transfer roll printing, or similar techniques. Preferably, both the Ag underlayer and the Ag/AgCl electrode are applied using a low temperature screen print onto a polymeric substrate. This low temperature screen print can be carried out at about 125 to 160° C., and the screening can be carried out using a suitable mesh, ranging from about 100–400 mesh.

In another preferred embodiment, the automatic sampling system transdermally extracts the sample in a continual manner over the course of a 1–24 hour period, or longer, using sonophoresis. More particularly, a source of ultrasonic radiation is coupled to the collection reservoir and used to provide sufficient perturbation of the target tissue surface to allow passage of the analyte (glucose) across the tissue surface. The source of ultrasonic radiation provides ultrasound frequencies of greater than about 10 MHz, preferably in the range of about 10 to 50 MHz, most preferably in the range of about 15 to 25 MHz. It should be emphasized that these ranges are intended to be merely illustrative of the preferred embodiment; in some cases higher or lower frequencies may be used.

The ultrasound may be pulsed or continuous, but is preferably continuous when lower frequencies are used. At very high frequencies, pulsed application will generally be preferred so as to enable dissipation of generated heat. The preferred intensity of the applied ultrasound is less than about 5.0 W/cm², more preferably is in the range of about 0.01 to 5.0 W/cm², and most preferably is in the range of 0.05 to 3.0 W/cm².

Virtually any type of device may be used to administer the ultrasound, providing that the device is capable of producing the suitable frequency ultrasonic waves required by the invention. An ultrasound device will typically have a power source such as a small battery, a transducer, and a means to attach the system to the sampling system collection reservoir. Suitable sonophoresis sampling systems are described in International Publication No. WO 91/12772, published Sep. 5, 1991, the disclosure of which is incorporated herein by reference.

As ultrasound does not transmit well in air, a liquid medium is generally needed in the collection reservoir to efficiently and rapidly transmit ultrasound between the ultrasound applicator and the tissue surface.

Figure 2:
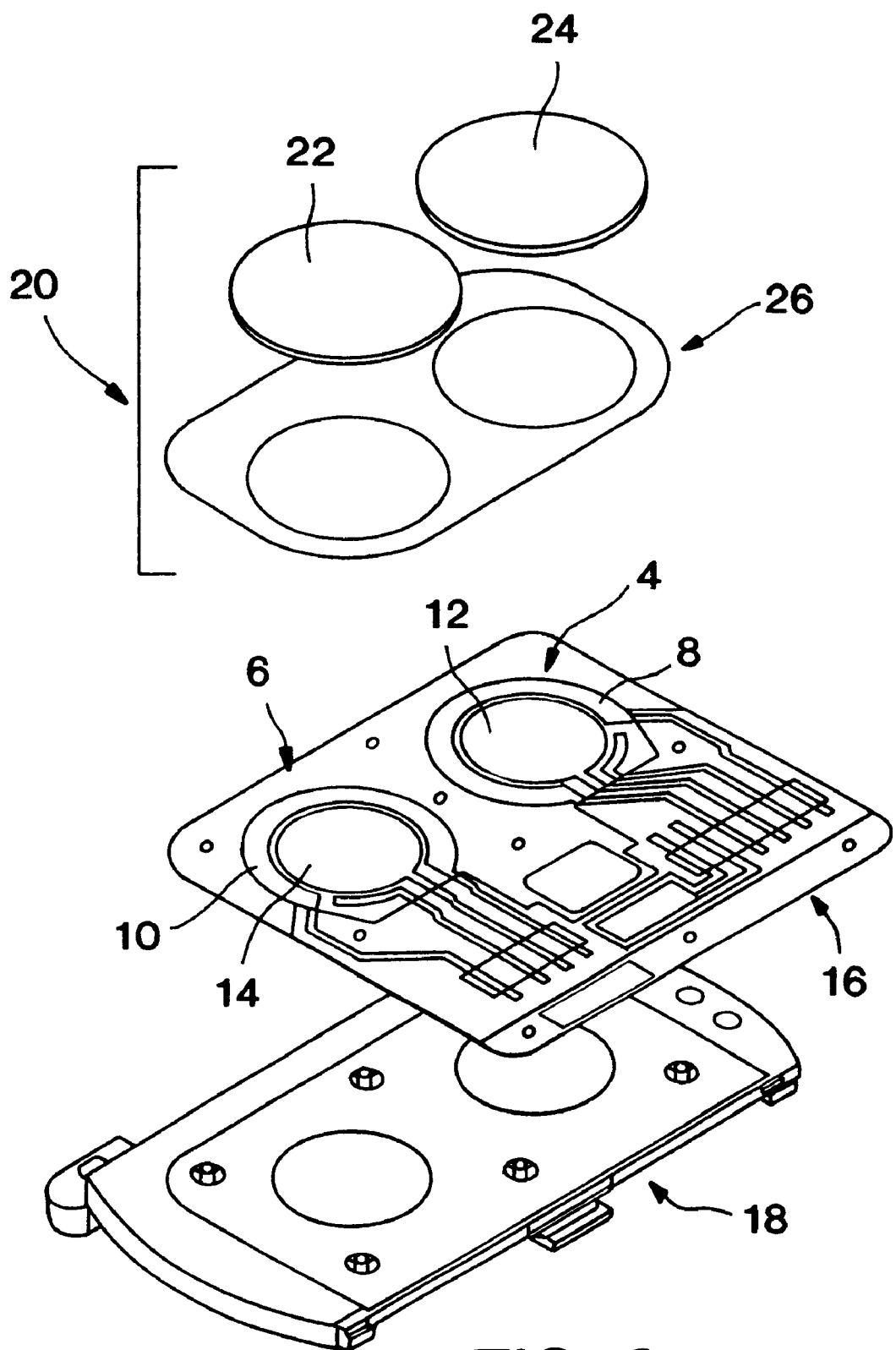
FIG. 2 is an exploded pictorial representation of components from a preferred embodiment of the automatic sampling system of the present invention.

Referring now to FIG. 2, an exploded view of the key components from a preferred embodiment of an iontophoretic sampling system is presented. The sampling system components include two biosensor/iontophoretic electrode assemblies, 4 and 6, each of which have an annular iontophoretic electrode, respectively indicated at 8 and 10, which encircles a biosensor 12 and 14. The electrode assemblies 4 and 6 are printed onto a polymeric substrate 16 which is maintained within a sensor tray 18. A collection reservoir assembly 20 is arranged over the electrode assemblies, wherein the collection reservoir assembly comprises two hydrogel inserts 22 and 24 retained by a gel retainer 26.

In one embodiment, the electrode assemblies can include bimodal electrodes as shown in FIG. 3 and described above.

The components shown in exploded view in FIG. 2 are intended for use in a automatic sampling system which is configured to be worn like an ordinary wristwatch. As described in International Publication No. WO 96/00110, published Jan. 4, 1996, the wristwatch housing (not shown) contains conductive leads which communicate with the iontophoretic electrodes and the biosensor electrodes to control cycling and provide power to the iontophoretic electrodes, and to detect electrochemical signals produced at the biosensor electrode surfaces. The wristwatch housing can further include suitable electronics (e.g., microprocessor, memory, display and other circuit components) and power sources for operating the automatic sampling system.

Modifications and additions to the embodiment of FIG. 2 will be apparent to those skilled in the art.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric.

All patents, patent applications, and publications mentioned herein, both supra and infra, are hereby incorporated by reference.

EXAMPLE 1

Assessing Background Noise and Sensitivity in a Biosensor

The following procedure can be used to determine the background current and sensitivity to hydrogen peroxide of a biosensor electrode in a glucose monitoring system.

Method: The sensitivity and background of the working biosensor electrode is determined by placing the biosensor in a test cell of fixed volume. The cell is filled with a pH 7.5 0.1 M phosphate buffered saline (PBS) solution containing 77 mM NaCl. The buffer solution is quiescent in the cell during measurement. The biosensor is then biased at the usual operating potential of 0.6V, and the steady-state background current measured. A 2 $\mu$M solution of hydrogen peroxide is then prepared in the same PBS buffer solution, and is added to the test cell. The biosensor is again biased, and the current measured at fixed time points. The measurement is repeated for 5 $\mu$M and 10 $\mu$M hydrogen peroxide solutions.

A calibration curve can be constructed from the currents obtained for the three hydrogen peroxide concentrations for the fixed time points. Because the currents decay over time after the sensor bias is applied, it is best to pick one standard time point (for example 60 seconds) to characterize the sensitivity of the biosensor to hydrogen peroxide.

The hydrogen peroxide solution should be made up within 2 hours of the test, and stored in an amber (or foil-covered) container until use to prevent decomposition of the hydrogen peroxide.

The following ingredients can be used to make up the PBS buffer (NaCl, $NaH_2PO_4 \cdot H_2O$, and $Na_2HPO_4 \cdot 7\ H_2O$). The recipe to make up this pH 7.5 buffer is as follows:

To make 2 liters of 0.05 M pH 7.5 phosphate-buffered saline (PBS): 2.20 g $NaH_2PO_4 \cdot H_2O + 22.5$ g $Na_2HPO_4 \cdot 7\ H_2O + 8.98$ g NaCl; add water to bring to 2 liters. The hydrogen peroxide solutions can be made from 3% stock solution which is stable if stored in the refrigerator.

EXAMPLE 2

Assessing Passive Hydrogen Peroxide Depletion in a Biosensor

The following procedure can be used to determine the rate of passive (non-electrochemical) hydrogen peroxide depletion caused by a biosensor electrode constructed in accordance with the present invention.

Method: The following procedure is optimized to test biosensor electrodes having an approximate geometric area of 1 $cm^2$, and a total biosensor area of about 3 $cm^2$; however, these methods are readily scalable to smaller or larger electrode dimensions by the ordinarily skilled artisan.

The biosensor to be tested is placed in a test cell which contains a volume of test solution of approximately 360 $\mu$L in contact with the electrode. The thickness of the solution layer in contact with the biosensor electrode is approximately 50 mil (0.127 cm). The body of the test cell is preferably made from materials that do not cause a substantial amount of hydrogen peroxide degradation, for example polytetrafluoroethylene (e.g., TEFLON®) or poly (chlorotrifluoroethylene) (e.g., Kel-F®). The test solution contains 20 $\mu$M hydrogen peroxide in 0.1 M PBS (pH 7.5) containing NaCl. The test solution is added to the cell and left in contact with the biosensor for 15 minutes. The test solution is withdrawn from the cell, and the remaining concentration of hydrogen peroxide is measured and compared to standard solutions that were not contacted with the biosensor. The concentration of hydrogen peroxide remaining in the test solution can then determined using several methods known to those of skill in the art, for example, by liquid chromatography or by one of several commercially available hydrogen peroxide test kits (e.g., PeroXOquant™, available from Pierce Chemical Co., Rockford Ill.).

Solid Pt biosensor electrodes tested in the above-described procedure generally exhibit from 55–75% passive (non-electrochemical) hydrogen peroxide degradation, whereas Pt-containing electrodes constructed according to the invention preferably exhibit from about 10–25% passive hydrogen peroxide degradation, and more preferably less than about 20% passive degradation.

EXAMPLE 3

Testing Protocol for Ag/AgCl Screen-Printed Electrodes

The following procedure can be used determine the amount of Ag and AgCl in a screen printed Ag/AgCl electrode that is electrochemically accessible at a given current density.

Method: The amount of available Ag and AgCl is determined by passing a constant current between the Ag/AgCl electrode and a counter electrode immersed in a suitable electrolyte until an increase in the applied voltage indicates that depletion of Ag or AgCl has occurred.

Test of available Ag: The Ag/AgCl electrode and a much larger counter electrode of chloridized silver foil are placed opposite each other in a beaker. The beaker is filled with 0.1 M PBS buffer (pH 7.5) containing 77 mM NaCl. The electrodes are connected to a suitable constant current power source and the electrodes biased so that the Ag/AgCl electrode is positive with respect to the counter electrode. A constant current passes between the electrodes. The applied potential is monitored and the amount of time required for the applied potential to reach 1.0 V is measured. (At 1.0 V, undesirable side reactions can start occurring.) The amount of charge which is passed is equal to the current times the number of seconds.

Test of available AgCl: The Ag/AgCl electrode and a much larger counter electrode of chloridized silver foil are placed opposite each other in a beaker. The beaker is filled with 0.1 M PBS buffer (pH 7.5) containing 77 mM NaCl. The electrodes are connected to a suitable constant current power source and the electrodes biased so that the Ag/AgCl electrode is negative with respect to the counter electrode. A constant current passes between the electrodes. The applied potential is monitored and the amount of time required for the applied potential to reach −1.0 V is measured. (At −1.0 V, undesirable side reactions can start occurring.) The amount of charge which is passed is equal to the current times the number of seconds.

A preferred Ag/AgCl iontophoresis electrode for use in the present invention to provide for a 24 hour period of continual sampling can have the following specifications: (1) an electrode area of about 0.85 $cm^2$; (2) current of 0.3 mA (current density: 0.35 mA/$cm^2$); (3) available Ag and AgCl requirement per electrode of 0.5 millicoulomb/$cm^2$ @ 0.9 mA; (4) time duration of current: 7.5 minutes in each direction per cycle; (5) total charge passage of 135 mC (in each of the anodic and cathodic directions for a total of 270 mC); and (6) capable of at least 48 anode/cathode cycles.

What is claimed is:

1. A sensor element comprising,
a sensing electrode that reacts electrochemically with hydrogen peroxide to provide a detectable signal, said sensing electrode comprising a platinum-group metal, a geometric surface area that ranges from about 0.1 to about 3 $cm^2$, a background current that ranges from about 2 to about 60 nA or less when measured in a buffer solution at 0.6V, and a sensitivity of at least about 6 to about 180 nA/$\mu$M of hydrogen peroxide when measured in a buffer solution at 0.6V.

2. The sensor element of claim 1, wherein said platinum-group metal is selected from the group consisting of platinum, palladium, rhodium, ruthenium, osmium, and iridium.

3. The sensor element of claim 2, wherein the sensing electrode comprises platinum.

4. The sensor element of claim 3, wherein the sensing electrode comprises platinum and graphite dispersed within a polymer matrix.

5. The sensor element of claim 4, wherein the sensing electrode is configured to provide a geometric surface area of about 0.5 to about 2 $cm^2$.

6. The sensor element of claim 5, wherein the sensing electrode is configured to provide a geometric surface area of about 1 $cm^2$.

7. The sensor element of claim 4, wherein the sensing electrode comprises about 3% to about 7% by weight of platinum.

8. The sensor element of claim 6, wherein the sensing electrode comprises a background current of about 20 nA when measured in a buffer solution at 0.6V, and a sensitivity of at least about 60 nA/μM of hydrogen peroxide when measured in a buffer solution at 0.6V.

9. The sensor element of claim 1, wherein the sensing electrode is printed onto a non-conductive rigid or flexible substrate.

10. The sensor element of claim 1, wherein the sensing electrode exhibits about 10% to about 25% passive hydrogen peroxide degradation.

11. The sensor element of claim 1, wherein the sensing electrode exhibits less than about 20% passive hydrogen peroxide degradation.

12. The sensor element of claim 1, wherein the sensor element further comprises a counter electrode and a reference electrode.

13. The sensor element of claim 12, wherein the counter electrode comprises Ag/AgCl.

14. The sensor element of claim 13, wherein the counter electrode is a bimodal electrode that functions non-simultaneously as the counter electrode and as an iontophoretic electrode.

15. The sensor element of claim 1, further comprising a collection reservoir wherein the sensing electrode is capable of quantifying an amount or concentration of analyte in the collection reservoir.

16. The sensor element of claim 15, wherein the collection reservoir comprises an ionically conductive material.

17. The sensor element of claim 15, wherein the collection reservoir comprises a hydrogel and the hydrogel comprises the ionically conductive material.

18. The sensor element of claim 17, wherein the ionically conductive material comprises one or more enzymes.

19. The sensor element claim 18, wherein at least one of the enzymes comprises glucose oxidase.

20. A method of making the sensor element of claim 1, comprising formulating a sensing electrode composition, said composition comprising a platinum-group metal and a binder; and affixing the sensing electrode composition to a non-conductive surface to provide the sensor element comprising the sensing electrode of claim 1.

21. The method of claim 20, wherein said sensing electrode composition comprises platinum and further comprises graphite.

22. The method of claim 21, further comprising before formulating said sensing electrode composition, (i) said platinum is sputtered onto a graphite powder, or (ii) said platinum is precipitated onto a graphite powder, or (iii) said platinum is adsorbed onto a graphite powder.

23. The method of claim 20, wherein the binder is an electrochemically inert polymer or resin.

24. The method of claim 20, wherein said affixing is accomplished using a thin-film technique.

25. The method of claim 20, wherein said affixing is accomplished using a thick-film technique.

26. The method of claim 20, wherein said affixing is accomplished using a method selected from the group consisting of screen printing, pad printing, inkjet printing, and transfer roll printing.

* * * * *

UNITED STATES PATENT AND TRADEMARK OFFICE
CERTIFICATE OF CORRECTION

PATENT NO. : 6,736,777 B2
DATED : May 18, 2004
INVENTOR(S) : Lynn Kim et al.

It is certified that error appears in the above-identified patent and that said Letters Patent is hereby corrected as shown below:

<u>Title page, Item [54] and Column 1, lines 1-3,</u>
Title, "BIOSENSOR, IONTOPHORETIC SAMPLING SYSTEM, AND METHODS OF USE THEREOF" should read -- SENSOR ELEMENT FOR MEASURING THE AMOUNT OR CONCENTRATION OF ONE OR MORE ANALYTES --;

<u>Column 22,</u>
Line 3, "element claim 18," should read -- element of claim 18, --.

Signed and Sealed this

Seventeenth Day of August, 2004

JON W. DUDAS
*Acting Director of the United States Patent and Trademark Office*